United States Patent [19]

Richard

[11] 4,236,526

[45] Dec. 2, 1980

[54] METHOD OF SCREENING FOR SICKLE CELL DISEASE BY DETECTION OF PORPHYRINS AND PORPHYRIN METABOLITES IN HUMAN DENTITION

[76] Inventor: Patricia A. Richard, 412 Gulf St., Milford, Conn.

[21] Appl. No.: 873,979

[22] Filed: Jan. 31, 1978

[51] Int. Cl.² .............................................. A61B 5/00
[52] U.S. Cl. .................................................. 128/633
[58] Field of Search .............. 128/2 R, 2 A, 633, 653, 128/663, 664; 23/230 B

[56] References Cited

U.S. PATENT DOCUMENTS

| | | | |
|---|---|---|---|
| 3,761,226 | 9/1973 | Louderback et al. | 23/230 B |
| 3,811,777 | 5/1974 | Chance | 128/653 X |
| 3,847,545 | 11/1974 | Shanbrom et al. | 23/230 B |
| 3,923,462 | 12/1975 | Cavanagh | 23/230 B X |

OTHER PUBLICATIONS

*Porphyrins*, by A. Vennotti, Hilger and Watts, Ltd., London, 1954, pp. 18, 19, 24, 25, 72 and 73.

*Hematology*, by Williams et al., McGraw-Hill, New York, 1972, pp. 452–453.
"The Kidney in Sickle Cell Disease: V", *Ghana Medical Journal*, vol. 12, No. 3, S. K. Addae, Sep., 1973, pp. 277–281.
*Burket's Oral Medicine Diagnosis and Treatment*, 7th ed., ed. by M. A. Lynch, J. B. Lippincott Co., Philadelphia, Toronto, 1977, pp. vii, xiv, xvi, 434–436, 770–773.

*Primary Examiner*—Richard T. Stouffer
*Attorney, Agent, or Firm*—DeLio and Montgomery

[57] ABSTRACT

A method of screening for sickle cell disease is provided by detecting the presence of porphyrins and porphyrin metabolites in human teeth comprising cleaning the teeth, exposing the cleaned teeth in vivo to a source of light, which has a wavelength known to excite the fluorescent emission spectrum characteristic of porphyrins and porphyrin metabolites and, optimally, which emits a wavelength of about 360 nm, detecting fluorescence, either visually or photographically, and determining the presence of porphyrins or porphyrin metabolites by emission of fluorescence characteristic thereto.

14 Claims, No Drawings

METHOD OF SCREENING FOR SICKLE CELL DISEASE BY DETECTION OF PORPHYRINS AND PORPHYRIN METABOLITES IN HUMAN DENTITION

DISCLOSURE OF THE INVENTION

BACKGROUND

The present invention pertains to the field of pathology and to a method for detection of products of systemic hemolysis and hepato-biliary disorders, namely porphyrins and porphyrin metabolites, deposited in human dentition. In particular, the invention is directed to providing a clinical method of screening patients for the occurrence of sickle cell disease in a manner which can be utilized in conjunction with routine dental examination.

The sickle cell disease, which encompasses the sickle cell trait and anemia associated therewith, is well known and is characteristically associated with red blood cells having an abnormal "sickle" shape. It is also well known that hemolysis of red blood cells is associated with sickle cell disease and occurs as a result thereof. As a consequence of hemolysis, porphyrins and porphyrin metabolites, in particular bilirubin and biliverdin, are released into the blood stream. While other pathological conditions can also cause hemolysis, for purposes of the invention it is sufficient to note that hemolysis, and the accompanying release of porphyrins and porphyrin metabolites, is well documented as an inherent characteristic associated with and indicative of sickle cell disease.

Porphyrins comprise a portion of hemoglobin, the major constituent of human red blood cells. Hemolysis involves the destruction of the red blood cell, which results in liberation of porphyrins in the blood stream. These porphyrins may subsequently be further broken down to bilirubin and biliverdin metabolites. It is known that porphyrins, as well as these porphyrin metabolites, will be absorbed and accumulate in the dentine of the teeth, as they are formed and calcified in the developing infant and child. Since sickle cell traits are passed genetically, porphyrins and porphyrin metabolites will be found in the patients possessing sickle cell disease and accumulate permanently in the dentition, as it develops.

Porphyrins are normally produced in the healthy body in connection with production of red blood cells, in which structures they are isolated and known as "hemato-porphyrins". A pathological condition termed porphyria is known in which the mechanism for production of hemato-porphyrins becomes uncontrolled and excess porphyrins are produced. These porphirins enter the blood stream and collect in certain parts of the body, depending upon the specific pathological condition experienced. In one rare type of porphyria, known as "congenital erythropoietic porphyria", high levels of porphyrins collect in the teeth. However, both as is recognized in the medical art and for purposes of this invention, the conditions involving porphyria and hemolysis associated with the sickle cell disease are different and distinct pathologies.

Likewise, the accumulations of porphyrins and porphyrin metabolites in various parts of the body, including the teeth, are different and distinguishable, not only in degree, but also as regards the levels which can accumulate and the fact that they have different systemic clinical manifestations. For example, congenital erythropoietic porphyria is readily distinguishable due to abnormal facial hair growth and extensive scarring on the skin, as well as a yellowish to reddish-brown discoloration of the teeth.

In the prior art, screening tests for the detection of sickle cell disease, as well as hepato-biliary disorders, have required that a specimen be obtained from the patient. Usually, either blood or urine specimens were obtained and examined either for the characteristically shaped sickle cells, in the case of a blood specimen, or the presence of porphyrins or porphyrin metabolites, in the case of urine analysis.

One significant disadvantage of these prior art techniques stems from the necessity of obtaining a specimen from the patient who, of course, must present himself or herself for submission of the specimen. Experience has shown that it can be difficult to successfully communicate to those individuals who may genetically be candidates for the sickle cell trait that it is necessary to submit to a special examination.

It is a particular advantage of the present invention that a method is provided whereby individuals, who genetically may be candidates for the sickle cell disease, can be clinically screened for its occurrence in conjunction with a routine dental examination. Since routine dental examinations are now widely available to most, if not all children, the present invention provides a method whereby the sickle cell traits can be identified much earlier then they might otherwise be detected later in life, when the anemic symptoms begin to manifest themselves outwardly in a more advanced stage of the disorder.

It is well known that porphyrins fluoresce with a characteristic red color, even in very low concentrations, under ultra-violet light, as set forth in *Porphyrins*, by A. Vannotti, Hilger & Watts Ltd., London, 1954, pages 18, 19, 24, 25, 72 and 73. Porphyrin metabolites, namely bilirubin and biliverdin, which result from the breakdown of porphyrin, are also known to fluoresce in the visual green range, usually about 500 nanometers (nm), when in the presence of zinc.

While the teeth are normally free from the presence or accumulation of porphyrins or the porphyrin metabolites, it is known that if porphyrin and its metabolites are present in the blood stream during the time the teeth form, they will be absorbed and accumulate in the dentine of teeth. As observed and reported by Williams et al, *Hematology*, p 452–453, McGraw-Hill, New York, 1972, discoloration of the teeth and emission of characteristic red fluorescence, under ultra-violet light, is a known phenomena associated with only the aforementioned congenital erythropoietic type of porphyria.

As indicated by Vannotti et al, the accumulation of porphyrins resulting from hemolysis in the dentine can be detected upon exposure of the tooth dentine to ultra-violet light. However, these observations were made with regard to in vitro study of tooth dentine, which lies inside the tooth enamel. Accordingly, there is no teaching or suggestion in the prior art that a clinical method could be developed for in vivo detection of the presence of porphyrins or porphyrin metabolites resulting from hemolysis or sickle cell disease.

Accordingly, the present invention provides a novel method for clinically screening for the presence of sickle cell disease or occurrence of hemolysis, through clinical in vivo examination of the tooth enamel. As a result, a highly advantageous advance in the art has been achieved, in that a method for detection of porphyrins or porphyrin metabolites is provided which does not require removal of a specimen from the patient, nor in vitro inspection of the tooth.

SUMMARY OF THE INVENTION

The invention provides a novel method for clinically screening the occurrence of sickle cell disease by detection of porphyrins or porphyrin metabolites produced by the hemolysis associated therewith.

The method involves an in vivo examination of teeth which do not indicate accumulations of porphyrins associated with congenital erythropoietic porphyria to detect the presence of porphyrins or porphyrin metabolites and comprises:

(a) cleaning the teeth,
(b) directing upon the cleaned teeth a source of light known to excite the fluorescent emission spectrum characteristic of porphyrins and porphyrin metabolites,
(c) detecting any fluorescence emitted from the surface of said teeth upon which such light is directed, and
(d) determining whether any fluorescence detected is characteristic of the emission spectrum known to be emitted by porphyrins or porphyrin metabolites under the influence of such light.

A positive result in detecting the presence of porphyrins or porphyrin metabolites indicates the occurrence of hemolysis and constitutes a positive screening test for the occurrence of sickle cell disease. Preferably, ultraviolet light having a wavelength of about 360 nanometers (nm) is utilized and may be obtained from a conventional source, such as a Wood's lamp, or may be provided by a tunable laser.

The method of the invention also can be utilized to screen patients for the occurrence of other hemolytic hepato-biliary disorders which produce porphyrins and porphyrin metabolites in the blood stream.

It is, therefore, a primary object of the invention to provide a clinical method for screening the occurrence of sickle cell disease, which is not only reliable, inexpensive and convenient to perform, but which may be conducted in connection with routine dental examination and avoid the requirement of extracting a specimen from the patient.

It is a further object of the invention to provide a clinical method for screening the occurrence of sickle cell disease which is safe and painless for the patient.

It is yet a further object of this invention to provide a method for detecting the occurrence of hemolysis, irrespective of whether it is caused by the occurrence of sickle cell disease or by the presence of other disorders involving hemolysis and the associated occurrence of porphyrin and porphyrin metabolites in the blood stream during the period when the teeth are developing in the patient.

The features of the invention which are believed to be novel are particularly set forth and distinctly claimed in the concluding portion of the specification. The invention, however, both as to its organization and operation, together with further objects and advantages thereof, may best be appreciated by reference to the following detailed description of the preferred embodiment and the appended claims.

DESCRIPTION OF THE PREFERRED EMBODIMENT

As used herein, the term "porphyrin" refers to the basic structure of all porphyrins which constitute the heme portion of the hemoglobin molecule of the red blood cell consisting of four pyrole rings joined in cyclic confirmation by four methine bridges.

As used herein, the term "porphyrin metabolites" refers to the products of the breakdown of porphyrins, including but not limited to bilirubin and biliverdin.

As used herein, the term "hemolysis" refers to the destruction of the red blood cell, as a consequence of which a porphyrin and/or porphyrin metabolites are liberated into the blood stream.

As used herein, the term "hepato-biliary disorders" refers to disorders pertaining to the liver, bile and gall bladder.

The term "dentine" as used herein refers to the portion of a tooth lying inside of the enamel surface. Likewise, the term "enamel" as used herein with reference to a tooth refers to the outer surface visable upon inspection of the oral cavity.

As used herein, the term "sickle cell disease" includes both the homozygote and heterozygote forms of the disease and refers to those individuals possessing and effected by the sickle cell gene determinant.

For purposes of this invention and as a convenient shorthand notation herein, all references to "excitation spectra light" encompass any light or electromagnetic radiation having a wavelength known to excite the fluorescent emission spectrum characteristic of porphyrins and porphyrin metabolites.

In accordance with the preferred embodiment of the invention a method for screening patients for the occurrence of sickle cell disease is provided involving in vivo examination of the teeth. It is intended to be performed clinically, in conjunction with routine dental examination of those individuals who are genetically susceptible to sickle cell disease. Of course, the method can only be utilized on patients whose teeth and other systemic manifestations do not indicate the extensive accumulations of porphyrins associated with the congenital erythropoietic porphyria.

In accordance with the preferred embodiment, the teeth are first cleaned, preferably applying an accepted acidulated prophy paste, followed by rinsing with water. Cleaning of the teeth is important. It not only removes any foreign material which might interfere with the detection of porphyrins or porphyrin metabolites, but it also provides a clean surface on the tooth enamel, so that there will be no interference with or reduction of the intensity of porphyrin or porphyrin metabolite fluorescence which occurs under the influence of ultra-violet light.

A source of excitation spectra light, preferably ultraviolet, is then directed upon the cleaned enamel surface of the teeth in the patient's oral cavity. The ultra-violet light should emit a wavelength of between about 275–400 nm and, optimally, a wavelength of 360 nm. The wavelength of 360 is preferred because of the strong intensity of the fluorescence produced. Nevertheless, it is within the purview of the invention that light of any wavelength, or wavelengths, which is known to produce a characteristic fluorescence upon exposure to porphyrins or porphyrin metabolites can be utilized. For example, green light (542 nm) also excites the desired emission spectra.

The next step in accordance with the preferred embodiment is to detect if any fluorescence is emitted from the surface of the teeth upon which the excitation spectra light is directed. Finally, any fluorescence detected is then evaluated and analyzed to determine whether it is the fluoresence characteristic of that known to be emitted by porphyrins or porphyrin metabolites.

A positive result in detecting the emission of fluorescence characteristic of that known to be emitted by porphyrins or porphyrin metabolites indicates their prescence in the tooth enamel and likewise constitutes a positive screening test for sickle cell disease. Of course, it is fully within the purview of the invention that such a positive result may also be indicative of other diseases and hepatobiliary disorders which also result in the release of porphyrins or porphyrin metabolites into the blood stream at a time when the patient's teeth are being formed.

The source of ultra-violet light used in accordance with the method of the invention may be any conventionally available apparatus. For example, the well-known Wood's lamp, which emits ultra-violet light having a wavelength of 360 nm, may conveniently be utilized and is readily available. However, it is fully contemplated that other sources of radiation generally in the range of about 480–590 nm can be utilized. For example, a tunable laser, the light emission of which can be adjusted to fall in the excitation spectra range can also be advantageously utilized.

A tunable laser is particularly useful, since it allows for selection of monochromatic light emission in the desired spectra. Thus, interference with undesirable wavelengths can be avoided.

Fluorescence emitted from the surface of the teeth under the influence of excitation spectra light may be detected visually. A characteristic red (590–700 nm) and near infra red (700–1100 nm) fluorescence is emitted by the porphyrins. A characteristic green (490–560 nm) fluorescence is emitted by the porphyrin metabolites, bilirubin and biliverdin which give a maximum emission peak of 500 nm in response to violet light of 435 nm.

Alternatively, fluorescence may be detected in any conventional manner and recorded accordingly. For example, either a photographic record of such fluorescence may be made, or its emission may be detected using a photomultiplier detector or like apparatus.

While porphyrins characteristically emit a red fluorescence, the fluorescence spectra is a function of pH. It is, however, within the purview of the invention that the fluorescence emitted from the enamel of teeth under excitation spectra light may be in the red-orange or orange-yellow band, if the pH is acid, or in the orange or extreme red band in conditions of neutral or alkaline pH in the oral cavity. Accordingly, while it is preferred to thoroughly clean and rinse the teeth before directing excitation spectra light thereupon, it is fully within the purview thereof that porphyrins may be detected through the fluorescence in the aforementioned bands, if the pH of the tooth enamel is other than neutral or alkaline. This could result from failure to clean the teeth prior to exposure to the excitation spectra light.

As already indicated, the immediate metabolic products of porphyrin, namely bilirubin and/or biliverdin, fluoresce in the visable green range in response to ultra-violet light. These metabolic products can either collect with or without porphyrins in the teeth or occur there as a result of a breakdown of porphyrins by long-term exposure to air and sunlight. Accordingly, detection of fluorescence in the green visable range may likewise constitute a positive test for the presence of products of hemolysis or hepato-biliary disorders.

For purposes of the invention, only low levels of exposure to the excitation spectra light should be utilized. In view of the sensitivity of the fluorescence of porphyrins and porphyrin metabolites, low levels of the excitation spectra light are fully sufficient to induce the sought-after fluorescence with sufficient intensity to be visably detectable. It is also possible to utilize a photodetector, either with or without the aid of a photo-multiplier, to detect lower fluorescent levels than is practical to detect visually. Such instrumental detection requires even lower levels of exposure to excitation spectra light than required for visual observation.

For purposes of the successful achievement of the objects of the invention and for the safety of the patient, it is recommended that the intensity of any ultra-violet light to which a patient is exposed be well within medically acceptable safe limits. While the method of the invention would be operable if the oral cavity was exposed to unacceptably high levels of ultra-violet radiation, the safety of the patient could be impaired. In addition, excessive exposure to ultra-violet radiation could over a time cause degradation of the porphyrin and porphyrin metabolites accumulated in the teeth and thereby interfere with the observation of a positive test results.

EXAMPLE

A 13 year old male, both of whom's parents were known to carry the sickle cell trait, was clinically examined in accordance with the method of the invention and screened for the occurrence of sickle cell disease.

The patient's teeth were first thoroughly cleaned in a conventional manner using an acidulated prophy paste. The teeth were then thoroughly rinsed with water. Ultra-violet light was directed into the oral cavity and upon the patient's teeth, in a darkened room. The source of ultra-violet light utilized was a conventional Wood's lamp, which provided ultra-violet light having a frequency of about 360 nm.

Fluorescence in the red visual range was detected by visual observation of the enamel of the patient's permanent teeth. This constituted a positive result indicating the presence of porphyrins deposited in the teeth enamel and likewise constituted a positive screening test for sickle cell disease in the patient.

The occurrence of sickle cell disease in the subject patient was verified through use of conventional analytical techniques. In addition, a full-mouth radiographic survey of the subject patient demonstrated normal contrast of the enamel and dentine, delayed eruption and osteoporosis typical of sickle cell disease.

Although the Example is given solely for purposes of illustration, it will be understood by those skilled in the art that the method of the invention may be altered, varied or modified without departing from the spirit and scope of the invention as defined by the appended claims.

What is claimed is:

1. A clinical method for detecting the presence of porphyrins and porphyrin metabolites associated with sickle cell disease, in a patient whose systemic manifestations do not indicate occurrence of congenital erythropoietic porphyria, comprising:

(a) cleaning the teeth of said patient, (b) exposing the outer surface of said cleaned teeth in vivo to a source of excitation spectra light, (c) detecting fluorescence, whereby the presence of said porphyrins or porphyrin metabolites is determined by emission of characteristic fluorescence which can be observed visually, and (d) determining the presence of sickle cell disease based on the results of said detection.

2. The method of claim 1 wherein the cleaning of said teeth includes application of a conventional acidulated prophy paste, followed by rinsing with water.

3. The method of claim 1 wherein said excitation spectra light is ultra-violet light having a wavelength in the range of about 275–400 nm.

4. The method of claim 1 wherein said source of excitation spectra light is a Wood's lamp emitting a wavelength of about 360 nm.

5. The method of claim 1 wherein said source of excitation spectra light is a tunable laser.

6. The method of claim 1 wherein said fluorescence is recorded and the presence of porphyrins or porphyrin metabolites is determined from examination of said record.

7. The method of claim 6 wherein said record is a photographic record.

8. A method for screening and detecting the occurrence of sickle cell disease in humans, whose systemic manifestations do not indicate occurrence of congenital erythropoietic porphyria, comprising in vivo examination of the teeth to detect the presence of porphyrins or porphyrin metabolites associated therewith; wherein said examination comprises the steps of:

(a) cleaning the teeth of said patient, (b) directing upon the outer surface of said cleaned teeth a source of light known to excite the fluorescence emission spectrum characteristic of porphyrins and porphyrin metabolites, (c) detecting any fluorescence emitted from the surface of said teeth upon which said light is directed, (d) determining whether said fluorescence is characteristic of that known to be admitted by porphyrins or porphyrin metabolites under the influence of said light, and (e) determining the presence of sickle cell disease based on the results of said detection, whereby a positive result in detecting the presence of said porphyrins or porphyrin metabolites indicates a positive screening test for the occurrence of sickle cell disease.

9. The method of claim 8 wherein the cleaning of said teeth includes application of a conventional acidulated prophy paste, followed by rinsing with water.

10. The method of claim 8 wherein said light is ultra-violet light having a wavelength in the range of about 275–400 nm.

11. The method of claim 8 wherein said source of ultra-violet light is a Wood's lamp emitting a wavelength of about 360 nm.

12. The method of claim 8 wherein said source of said light is a tunable laser.

13. The method of claim 8 wherein said fluorescence detected is recorded and the presence of porphyrins or porphyrin metabolites is determined by examination of said record.

14. The method of claim 13 wherein said record is a photographic record.

* * * * *